(12) United States Patent
Sodeyama

(10) Patent No.: US 12,611,187 B2
(45) Date of Patent: Apr. 28, 2026

(54) ULTRASOUND DIAGNOSTIC APPARATUS FOR REDUCING INFLUENCES OF STRUCTURE AND SPECKLE IN SUBJECT

(71) Applicant: FUJIFILM Healthcare Corporation, Chiba (JP)

(72) Inventor: Aya Sodeyama, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 116 days.

(21) Appl. No.: 18/534,704

(22) Filed: Dec. 10, 2023

(65) Prior Publication Data

US 2024/0188934 A1     Jun. 13, 2024

(30) Foreign Application Priority Data

Dec. 13, 2022     (JP) ................................. 2022-198831

(51) Int. Cl.
*A61B 8/00*          (2006.01)
(52) U.S. Cl.
CPC .......... *A61B 8/5207* (2013.01); *A61B 8/5269* (2013.01)
(58) Field of Classification Search
None
See application file for complete search history.

(56) References Cited

U.S. PATENT DOCUMENTS

| | | | |
|---|---|---|---|
| 10,932,750 B2 | 3/2021 | Kanayama | |
| 11,123,044 B2 | 9/2021 | Kanayama | |
| 11,801,033 B2 | 10/2023 | Kanayama | |

| | | | |
|---|---|---|---|
| 2016/0317126 A1* | 11/2016 | Miyaki | ..................... A61B 8/12 |
| 2016/0367225 A1* | 12/2016 | Ichikawa | ................. A61B 8/14 |
| 2017/0007211 A1* | 1/2017 | Ichikawa | ............. A61B 8/5269 |
| 2017/0143300 A1* | 5/2017 | Kozai | ................. G01S 7/52033 |
| 2017/0150948 A1 | 6/2017 | Kanayama | |
| 2017/0258438 A1 | 9/2017 | Kanayama | |
| 2018/0064423 A1* | 3/2018 | Kawashima | ......... A61B 8/5292 |
| 2018/0271478 A1* | 9/2018 | Kozai | ...................... A61B 8/12 |
| 2019/0266732 A1* | 8/2019 | Perrey | ....................... G06T 7/20 |
| 2019/0336106 A1* | 11/2019 | Kozai | ................... A61B 8/5207 |
| 2020/0268355 A1 | 8/2020 | Watanabe et al. | |

FOREIGN PATENT DOCUMENTS

| | | |
|---|---|---|
| JP | 2005152422 | 6/2005 |
| JP | 2017093913 | 6/2017 |
| JP | 2017158917 | 9/2017 |
| JP | 2020138017 | 9/2020 |

* cited by examiner

*Primary Examiner* — Nyrobi Celestine
(74) *Attorney, Agent, or Firm* — JCIPRNET

(57)          ABSTRACT

Based on at least one of a degree of variation in brightness values of pixels or a representative brightness value of frame data for evaluation range decision for each region defined in a data space of frame data, each region is classified into a region that is included in an evaluation range and a region that is not included in the evaluation range. An attenuation amount estimation unit estimates an attenuation amount of ultrasound waves in a subject based on a frequency spectrum of reception beam data of each region included in the evaluation range among a plurality of regions arranged in a depth direction, the region being defined in a data space of the reception beam data and corresponding to each region defined in the data space of the frame data. An image formation unit executes TGC processing as brightness correction processing based on the attenuation amount of the ultrasound waves estimated by the attenuation amount estimation unit.

8 Claims, 11 Drawing Sheets

ULTRASOUND DIAGNOSTIC APPARATUS FOR REDUCING INFLUENCES OF STRUCTURE AND SPECKLE IN SUBJECT

CROSS-REFERENCE TO RELATED APPLICATION

This application claims the priority benefits of Japanese application no. 2022-198831, filed on Dec. 13, 2022. The entirety of the above-mentioned patent application is hereby incorporated by reference herein and made a part of this specification.

BACKGROUND

1. Technical Field

The present disclosure discloses an improvement of an ultrasound diagnostic apparatus.

2. Description of the Related Art

In the related art, an ultrasound diagnostic apparatus has been known, which transmits and receives ultrasound waves to and from a subject, forms an ultrasound image based on a reception signal obtained by transmitting and receiving the ultrasound waves, and displays the formed ultrasound image on a display. The ultrasound image that can be formed by the ultrasound diagnostic apparatus includes a tomographic image (B-mode image) that is formed by transforming the signal intensity (amplitude) of the reception signal into a brightness value.

The ultrasound waves transmitted to the subject is attenuated in the subject. Therefore, the signal intensity of the reflected waves reflected from a deep part of the subject (place farther from a body surface) is smaller than the signal intensity of the reflected waves reflected from a shallow part. Then, in the B-mode image, the brightness of the pixel in the deep part is smaller than the brightness of the pixel in the shallow part.

In order to correct this phenomenon, in the related art, time gain control (TGC) of correcting the signal intensity of the reflected waves according to the depth of the subject is performed.

For example, JP2005-152422A discloses an ultrasound image formation apparatus that can calculate a histogram for each brightness value of each pixel of an ultrasound image, obtain a cumulative histogram obtained by cumulating the histograms of the respective brightness values, and automatically perform TGC with a gain correction value obtained such that the cumulative histogram passes through predetermined frequency value and brightness value.

JP2017-158917A, JP2017-093913A, and JP2020-138017A also disclose an ultrasound diagnostic apparatus having a TGC function. It should be noted that, JP2017-158917A, JP2017-093913A, and JP2020-138017A describe that a position of a structure (for example, organ) of a subject in the ultrasound image is estimated based on an average value and a variance value of the pixel values (brightness values) for each of a plurality of regions set in an ultrasound image (B-mode image).

SUMMARY

Noise called a speckle is generated in the B-mode image that is the ultrasound image in some cases. The speckle is an image of a stripe pattern generated by interference of scattered waves generated at an unspecified larger number of places in the subject with each other. Therefore, in a case in which the TGC is automatically performed by analyzing the brightness of each pixel of the B-mode image (in a case in which the gain correction value of the TGC is automatically decided), there is a case in which an appropriate TGC cannot be executed due to the influence of the speckle.

In addition, in a region corresponding to the structure (for example, organ or blood vessel) in the subject in the B-mode image, the brightness value may be high (or low conversely) due to a constitution of the structure. In addition, in the structure in the subject, there is a case in which the attenuation of the ultrasound waves is not so much generated as compared with other positions. Therefore, it is desirable to reduce the influence of the structure of the subject in the automatic TGC.

An object of an ultrasound diagnostic apparatus disclosed in the present specification is to execute suitable automatic time gain control in which influences of a structure and a speckle in a subject are reduced.

An aspect of the present specification relates to an ultrasound diagnostic apparatus comprising: an evaluation range decision unit that analyzes frame data for evaluation range decision formed based on beam data for evaluation range decision, which is reception beam data formed by reception beam forming with respect to a reception signal obtained by transmitting and receiving ultrasound waves to and from a subject, to decide an evaluation range excluding at least a part of a structure in the subject in a data space of frame data; an attenuation amount estimation unit that estimates an attenuation amount of the ultrasound waves based on target beam data before detection processing out of target beam data that are reception beam data following the beam data for evaluation range decision in time series, the attenuation amount estimation unit estimating the attenuation amount of the ultrasound waves based on a frequency spectrum of the target beam data before the detection processing of each region included in the evaluation range among a plurality of regions arranged in a depth direction of the subject defined in advance in a data space of the reception beam data, without using the target beam data of the region that is not included in the evaluation range; and an image formation unit that forms an ultrasound image based on the target beam data while executing brightness correction processing of correcting, to compensate for brightness of a pixel of the ultrasound image which is decreased due to attenuation of the ultrasound waves, the brightness of each pixel based on the estimated attenuation amount.

With this configuration, the evaluation range decision unit excludes the region including the structure in the subject from the evaluation range that is a target for estimating the attenuation amount of the ultrasound waves. As a result, the influence of the structure in the subject in the brightness correction processing is reduced. Further, with this configuration, the attenuation amount estimation unit calculates the frequency spectrum of the reception beam data for each region having a certain width, and estimates the attenuation amount of the ultrasound image based on the frequency spectra of the plurality of regions arranged in the depth direction. As a result, the influence of the speckle in the brightness correction processing is reduced.

The evaluation range decision unit may decide the evaluation range based on, for each region in the data space of the frame data corresponding to each region in the data space of the reception beam data, at least one of a degree of variation in brightness values of a plurality of pixels included in the region in the frame data for evaluation range decision or a representative brightness value of the plurality of pixels included in the region.

The attenuation amount estimation unit may estimate the attenuation amount based on at least one of a frequency integrated value of signal intensity in the frequency spectrum, a signal intensity slope representing a degree of decrease of the signal intensity toward a high frequency side in the frequency spectrum, a cross point frequency that is a frequency at which signal intensity of a signal component and signal intensity of a noise component in the frequency spectrum are the same as each other, or a representative frequency of the signal component in the frequency spectrum of each region arranged in the depth direction.

The attenuation amount estimation unit may estimate the attenuation amount for each region row arranged in the depth direction, to estimate a frame attenuation amount corresponding to one entire frame based on a plurality of the attenuation amounts estimated for a plurality of the region rows for one frame.

With this configuration, in a case in which the attenuation amounts of the ultrasound waves calculated for each region row arranged in the depth direction are different from each other, in the ultrasound image after the brightness correction processing, it is possible to suppress the brightness correction value from being different for each region row arranged in the depth direction.

The attenuation amount estimation unit may estimate the frame attenuation amount based on a plurality of individual frame attenuation amounts for each of a plurality of frames.

With this configuration, it is possible to estimate the frame attenuation amount in consideration of an error between the individual frame attenuation amounts for each frame.

The attenuation amount estimation unit may decide the individual frame attenuation amount used for estimating the frame attenuation amount among the plurality of individual frame attenuation amounts based on statistics of the plurality of individual frame attenuation amounts for each of the plurality of frames.

With this configuration, it is possible to estimate the frame attenuation amount by excluding the individual frame attenuation amount that is unlikely to indicate the correct attenuation amount of the ultrasound waves.

The image formation unit may execute the brightness correction processing at a timing at which an instruction is given from a user.

With this configuration, the user can execute the brightness correction processing at any timing, and can suppress flicker (temporal change in the brightness value) of the B-mode image.

The image formation unit may execute the brightness correction processing in a case in which it is determined that a posture of an ultrasound probe that transmits and receives the ultrasound waves to and from the subject is stable.

With this configuration, it is possible to automatically execute the brightness correction processing in a case in which the user brings the ultrasound probe into contact with a target position of the subject and maintains the contact.

With the ultrasound diagnostic apparatus disclosed in the present specification, it is possible to execute suitable automatic time gain control in which the influences of the structure and the speckle in the subject are reduced.

DESCRIPTION OF THE EMBODIMENTS

Schematic Configuration of Ultrasound Diagnostic Apparatus

Figure 1:
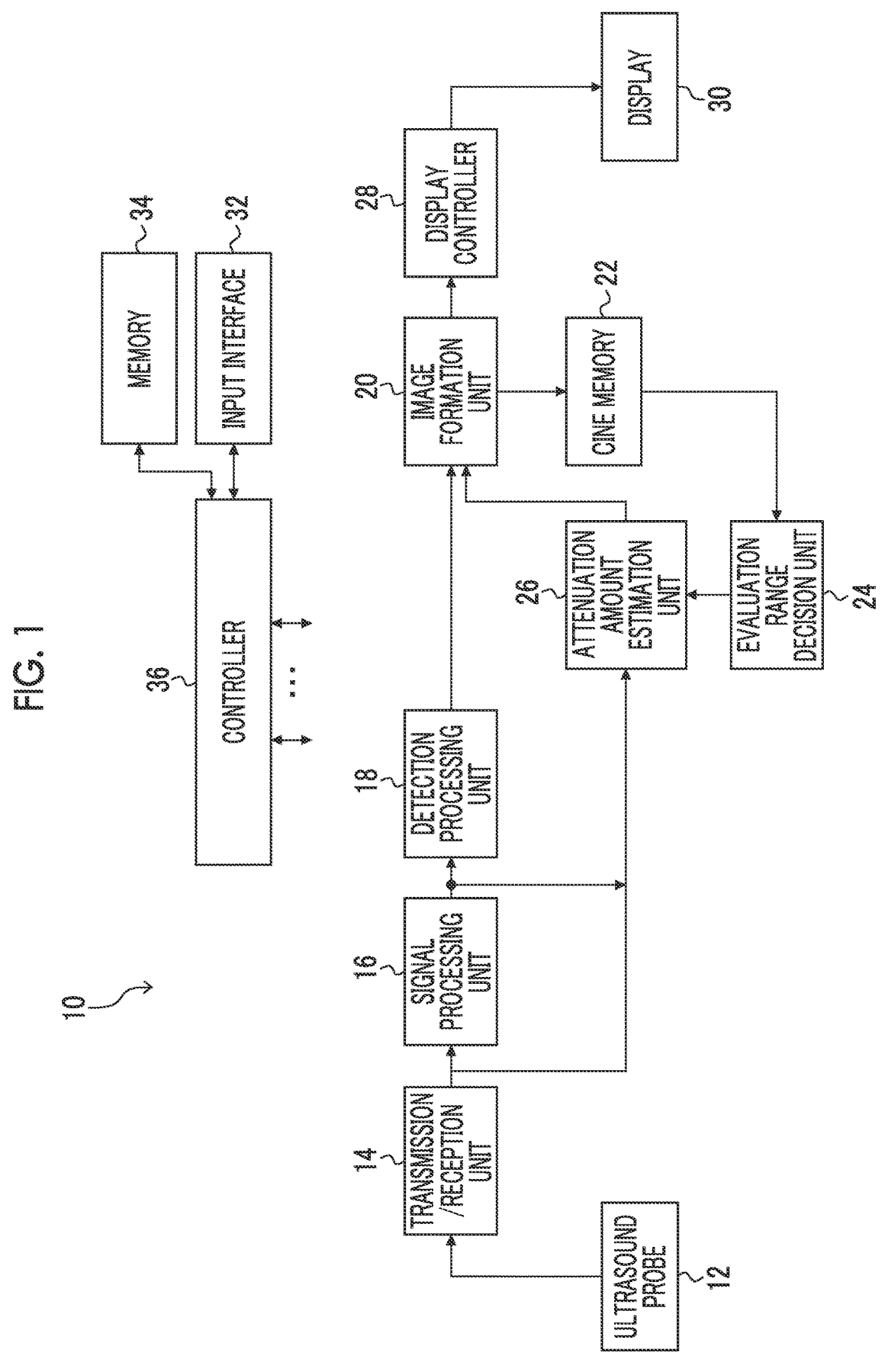
FIG. 1 is a schematic configuration diagram of an ultrasound diagnostic apparatus according to the present embodiment.

FIG. 1 is a schematic configuration diagram of an ultrasound diagnostic apparatus 10 according to the present embodiment. The ultrasound diagnostic apparatus 10 is a medical apparatus that is installed in a medical institution, such as a hospital, and is used during an ultrasound examination.

The ultrasound diagnostic apparatus 10 is an apparatus that scans a subject with an ultrasound beam to generate an ultrasound image based on a reception signal obtained by the scanning. For example, the ultrasound diagnostic apparatus 10 forms a tomographic image (B-mode image) in which the amplitude intensity of reflected waves from a scanning surface is transformed into the brightness based on the reception signal. Alternatively, the ultrasound diagnostic apparatus 10 can also form a Doppler image, which is an ultrasound image showing a motion velocity of a tissue in the subject, based on a difference (Doppler shift) between frequencies of transmitted waves and received waves. In the present embodiment, processing of generating the B-mode image by the ultrasound diagnostic apparatus 10 will be described.

An ultrasound probe 12 is a device that transmits and receives ultrasound waves to and from the subject. The ultrasound probe 12 has an oscillation element array including a plurality of oscillation elements that transmit and receive the ultrasound waves to and from the subject. An acceleration sensor may be provided in the ultrasound probe 12. A detection signal of the acceleration sensor is transmitted to an apparatus main body, whereby the apparatus main body can detect a posture of the ultrasound probe 12.

A transmission/reception unit 14 transmits a transmission signal to the ultrasound probe 12 (specifically, each oscillation element of the oscillation element array) under the control of a controller 36 (described later). As a result, the ultrasound waves are transmitted from each oscillation element toward the subject. In addition, the transmission/reception unit 14 receives a reception signal from each oscillation element that receives the reflected waves from the subject. The transmission/reception unit 14 includes an adder and a plurality of delayers corresponding to the respective oscillation elements, and phase adjustment addition processing of aligning and adding phases of the reception signals from the respective oscillation elements is performed by the adder and the plurality of delayers. As a result, reception beam data in which information indicating the signal intensity of the reflected waves from the subject is arranged in a depth direction of the subject is formed. Processing of forming the reception beam data is referred to as reception beam forming.

The transmission/reception unit 14 sequentially transmits the ultrasound waves to the subject based on the transmission signals sequentially transmitted from the controller 36. As a result, the transmission/reception unit 14 sequentially acquires the reflected waves from the subject, and forms the reception beam data. In this way, the transmission/reception unit 14 forms a plurality of time series reception beam data.

The signal processing unit 16 executes various types of signal processing including, for example, filter processing of applying a bandpass filter to the reception beam data from the transmission/reception unit 14.

The reception signal (reception beam data) after the reception beam forming by the transmission/reception unit 14 or the reception signal after the filter processing by the signal processing unit 16 is transmitted to an attenuation amount estimation unit 26 described later.

A detection processing unit 18 executes processing, such as detection processing (for example, envelope detection processing) or logarithmic compression processing, with respect to the reception signal after the processing by the signal processing unit 16. The reception signal loses the phase information (frequency information) due to the detection processing by the detection processing unit 18. That is, an amount of information of the reception signal after the detection processing is smaller than an amount of information of the reception signal before the detection processing.

An image formation unit 20 forms the ultrasound image (B-mode image) based on the reception beam data subjected to the detection processing or the like by the detection processing unit 18. In particular, the image formation unit 20 forms one B-mode image based on the reception beam data for one frame. In the present specification, the reception beam data for one frame or one B-mode image itself is referred to as frame data. In addition, the image formation unit 20 executes TGC processing as brightness correction processing based on the attenuation amount of the ultrasound waves estimated by the attenuation amount estimation unit 26 described later. As described above, the TGC processing is processing of correcting, to compensate for the brightness of the pixel of the ultrasound image which is decreased due to the attenuation of the ultrasound waves, the brightness of each pixel. Image quality enhancement processing of the ultrasound image by the image formation unit 20 will be described later.

The B-mode image formed by the image formation unit 20 is transmitted to a cine memory 22 and a display controller 28.

The cine memory 22 is a ring buffer that temporally stores one or a plurality of frame data. In the present embodiment, the cine memory 22 stores one or a plurality of B-mode images as the frame data, but the cine memory 22 may store the reception beam data for one or a plurality of frames as the frame data.

The evaluation range decision unit 24 analyzes the frame data stored in the cine memory 22 to decide an evaluation range excluding at least a part of a structure in the subject in the data space of the frame data. The structure in the subject in the present specification adversely affects (decreases the accuracy of an estimated attenuation amount) in estimating an attenuation amount of the ultrasound waves in the subject. That is, in the structure, the method of attenuating the ultrasound waves transmitted to the structure is different from a normal method (method of attenuating in a part other than the structure). Examples of the structure include an organ or a blood vessel.

In the present specification, the frame data that is an analysis target of the evaluation range decision unit 24 is referred to as frame data for evaluation range decision. As described above, in the present embodiment, the frame data for evaluation range decision is the B-mode image, but the frame data for evaluation range decision may be the reception beam data for one frame. Further, the reception beam data for generating the frame data for evaluation range decision is referred to as reception beam data for evaluation range decision. Details of the processing of the evaluation range decision unit 24 will be described later.

The attenuation amount estimation unit 26 estimates the attenuation amount of the ultrasound waves in the subject based on the target beam data before the detection processing out of the reception beam data (referred to as target beam data in the present specification) that are reception beam data following the reception beam data for evaluation range decision in time series. In particular, the attenuation amount estimation unit 26 estimates the attenuation amount of the ultrasound waves in the subject by using the target reception beam data included in the evaluation range without using the target reception beam data that is not included in the evaluation range decided by the evaluation range decision unit 24. Details of the processing of the attenuation amount estimation unit 26 will be described later.

A display controller 28 performs control of displaying, on a display 30, the ultrasound image formed by the image formation unit 20 and various types of other information. The display 30 is, for example, a display device configured of a liquid crystal display, an organic electro luminescence (EL), or the like.

An input interface 32 is configured of, for example, a button, a track ball, a touch panel, or the like. The input interface 32 is used to input a command from a user to the ultrasound diagnostic apparatus 10.

A memory 34 includes a hard disk drive (HDD), a solid state drive (SSD), an embedded multi media card (eMMC), a read only memory (ROM), or the like. The memory 34 stores an ultrasound diagnostic program for operating each of the units of the ultrasound diagnostic apparatus 10. It should be noted that the ultrasound diagnostic program can also be stored, for example, in a computer-readable non-transitory storage medium, such as a universal serial bus (USB) memory or a CD-ROM. The ultrasound diagnostic apparatus 10 can read and execute the ultrasound diagnostic program from such a storage medium.

The controller 36 includes at least one of a general-purpose processor (for example, a central processing unit (CPU)) or a dedicated processor (for example, a graphics processing unit (GPU), an application specific integrated circuit (ASIC), a field-programmable gate array (FPGA), a programmable logic device, and the like). The controller 36 may be configured by the cooperation of a plurality of processing devices that are present at physically separated positions, instead of being configured of one processing device. The controller 36 controls each of the units of the ultrasound diagnostic apparatus 10 according to the ultrasound diagnostic program stored in the memory 34.

It should be noted that each of the units of the transmission/reception unit 14, the signal processing unit 16, the detection processing unit 18, the evaluation range decision unit 24, the attenuation amount estimation unit 26, the image formation unit 20, and the display controller 28 is configured of one or a plurality of processors, chips, electric circuits, or the like. Each of these units may be realized by the cooperation between hardware and software.

The schematic configuration of the ultrasound diagnostic apparatus 10 is described above. Hereinafter, the details of the TGC processing based on the decided attenuation amount by the evaluation range decision unit 24, the attenuation amount estimation unit 26, and the image formation unit 20 will be described.

Decision of Evaluation Range

Figure 2:
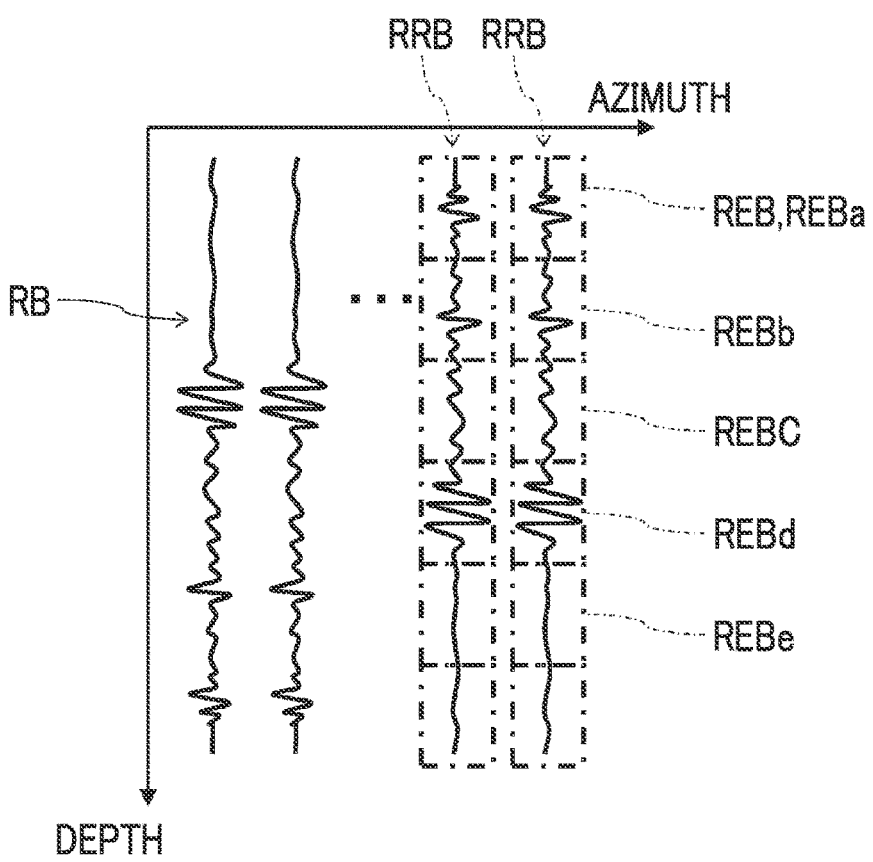
FIG. 2 is a conceptual diagram showing reception beam data and a region of the reception beam data in a data space.
Figure 3:
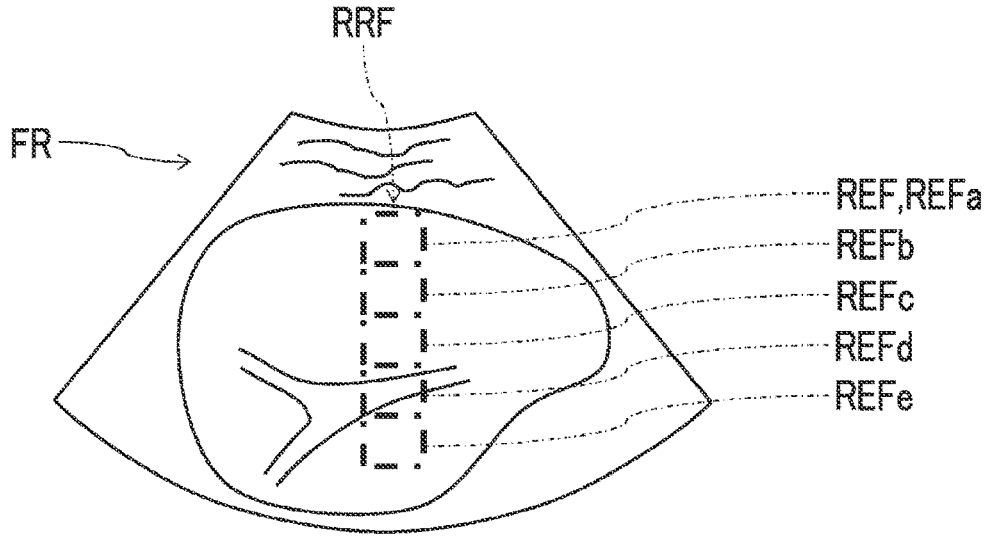
FIG. 3 is a conceptual diagram showing a region in a data space of frame data.

FIG. 2 is a conceptual diagram showing reception beam data RB formed by the reception beam forming by the transmission/reception unit 14 and a region REB defined in advance in the data space of the reception beam data RB. Further, FIG. 3 is a conceptual diagram showing a region REF defined in advance in a data space of frame data FR. A plurality of regions REB are defined in advance in the data space of the reception beam data RB as shown in FIG. 2, and a plurality of regions REF are defined in the data space of the frame data FR as shown in FIG. 3. One region REB and one region REF have a certain width (width corresponding to a plurality of pixels in the corresponding ultrasound image). The region REB of the reception beam data RB in the data space and the region REF of the frame data FR in the data space have a one-to-one correspondence with each other. For example, a region REBa corresponds to a region REFa, a region REBb corresponds to a region REFb, and the like.

In particular, in the data space of the reception beam data RB, a plurality of depth direction region rows RRB formed of the plurality of regions REB arranged in the depth direction are defined (in FIG. 2, only a part of the plurality of depth direction region rows RRB is shown). Therefore, also in the data space of the frame data FR, a plurality of depth direction region rows RRF formed of the plurality of regions REF arranged in the depth direction are defined (in FIG. 3, only a part of the plurality of depth direction region rows RRF is shown). The plurality of depth direction region rows RRB and RRF are arranged in an azimuth direction.

The evaluation range decision unit 24 calculates a degree of variation in the brightness values of a plurality of pixels included in the region REF for each region REF in the frame data for evaluation range decision. In the present embodiment, the evaluation range decision unit 24 calculates a standard deviation as the degree of variation. However, an indicator indicating the degree of variation is not limited to the standard deviation, and may be, for example, a variance value. In addition, the evaluation range decision unit 24 calculates a representative brightness value of the brightness values of the plurality of pixels included in the region REF for each region REF in the data space of the frame data FR. In the present embodiment, the evaluation range decision unit 24 calculates an average brightness value as the representative brightness value. However, the representative brightness value is not limited to the average brightness value, and may be, for example, a median brightness value.

The evaluation range decision unit 24 classifies each region REF into a region REF that is included in the evaluation range and a region REF that is not included in the evaluation range based on at least one of the degree of variation in the brightness values of the plurality of pixels included in the region REF in the frame data for evaluation range decision for each region REF defined in the data space of the frame data FR or the representative brightness value of the brightness values of the plurality of pixels included in the region REF. It should be noted that, in FIG. 3, the regions REFa, REFb, REFc, and REFe are regions REF that do not include the structure of the subject and should be included in the evaluation range, and the region REFd is the region REF that includes the structure (here, blood vessel) of the subject and should be excluded from the evaluation range.

For the region REF that does not include the structure of the subject, such as the regions REFa, REFb, REFc, and REFe, the degree of variation in the brightness values of the pixels included in the region REF is decreased. On the other hand, for the region REF including the structure of the subject, such as the region REFd, since ultrasound waves are strongly reflected at a boundary of the structure or the like, the degree of variation in the brightness values of the pixels included in the region REF is increased. Therefore, the evaluation range decision unit 24 sets the region REF in which the degree of variation in the brightness values is less than a predetermined variation threshold value as the region REF within the evaluation range, and sets the region REF in which the degree of variation in the brightness values is equal to or larger than the variation threshold value as the region REF outside the evaluation range.

In addition, in a case in which the region REF is included in the blood vessel that is the structure, the representative brightness value of the plurality of pixels included in the region REF is extremely decreased. Therefore, the evaluation range decision unit 24 may set the region RFE in which the representative brightness value is equal to or larger than a predetermined brightness threshold value as the region REF within the evaluation range, and set the region RFE in which the representative brightness value is less than the predetermined brightness threshold value as the region REF outside the evaluation range.

As described above, the evaluation range decision unit 24 analyzes the frame data for evaluation range decision to classify each region REF into the region REF included in the evaluation range and the region REF that is not included in the evaluation range. As described above, since each region REF in the data space of the frame data FR and each region REB in the data space of the reception beam data RB correspond to each other, the classification into the region REF included in the evaluation range and the region REF that is not included in the evaluation range means classifying each region REB into the region REB included in the evaluation range and the region REB that is not included in the evaluation range in the data space of the reception beam data RB.

Estimation of Attenuation Amount

First, the attenuation amount estimation unit 26 executes frequency analysis processing (for example, fast Fourier transform (FFT)) for each region REB with respect to the target beam data before the detection processing out of the target beam data that are the reception beam data RB following the beam data for evaluation range decision in time series. As a result, the frequency spectrum of the target beam data is acquired for each region REB. Next, the attenuation amount estimation unit 26 estimates the attenuation amount of the ultrasound waves based on the frequency spectrum of the target beam data of the region REB included in the evaluation range among the plurality of regions REB (that is, the depth direction region row RRB) which are defined in the data space of the reception beam data RB and arranged in the depth direction of the subject, without using the frequency spectrum of the target beam data of the region REB that is not included in the evaluation range decided by the evaluation range decision unit 24. Hereinafter, the estimation method of the attenuation amount of the ultrasound waves based on the frequency spectrum of the target beam data of the region REB included in the evaluation range will be described in detail.

The attenuation amount estimation unit 26 can estimate the attenuation amount of the ultrasound waves based on a frequency integrated value of the signal intensity in the frequency spectrum of the region REB which is the depth direction region row RRB (that is, the plurality of regions REB arranged in the depth direction) and included in the evaluation range. FIGS. 4A to 4E are diagrams showing a frequency integrated value I of the frequency spectrum for each of regions REBa to REBe shown in FIG. 2. The frequency integrated value I of each frequency spectrum is represented by an area of a shaded region in FIGS. 4A to 4E. It should be noted that, as shown in FIG. 2 or 3, the depth is increased from the region REBa toward the region REBe.

Figure 4A:
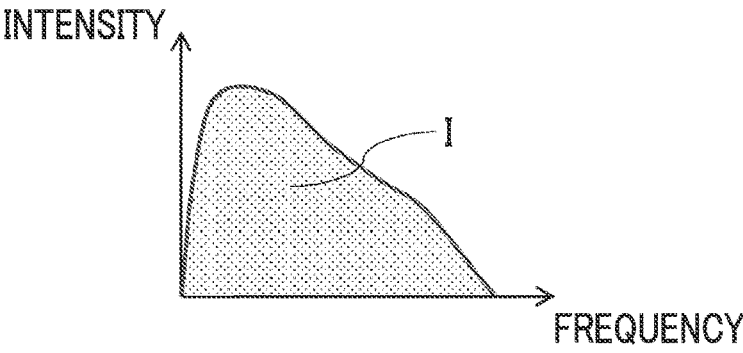
FIG. 4A is a diagram showing a frequency integrated value of a frequency spectrum in a region REBa of FIG. 2.
Figure 4B:
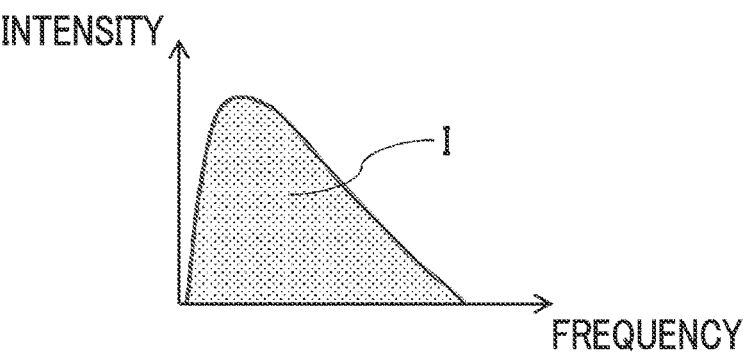
FIG. 4B is a diagram showing a frequency integrated value of a frequency spectrum in a region REBb of FIG. 2.
Figure 4C:
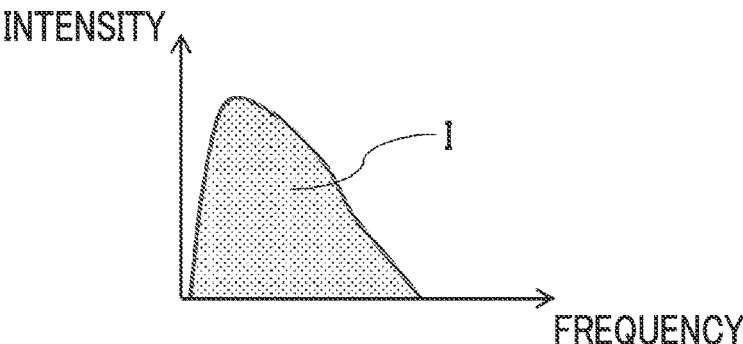
FIG. 4C is a diagram showing a frequency integrated value of a frequency spectrum in a region REBc of FIG. 2.
Figure 4D:
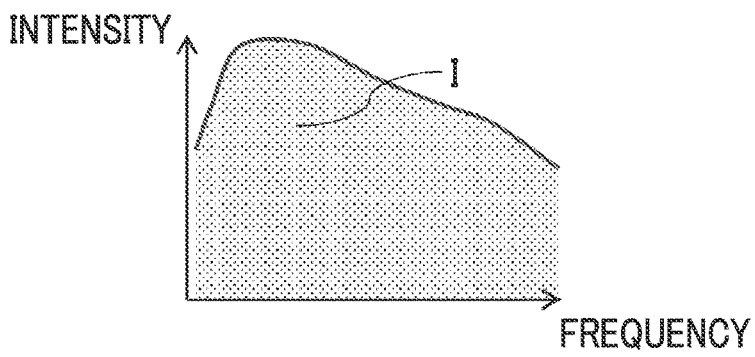
FIG. 4D is a diagram showing a frequency integrated value of a frequency spectrum in a region REBd of FIG. 2.
Figure 4E:
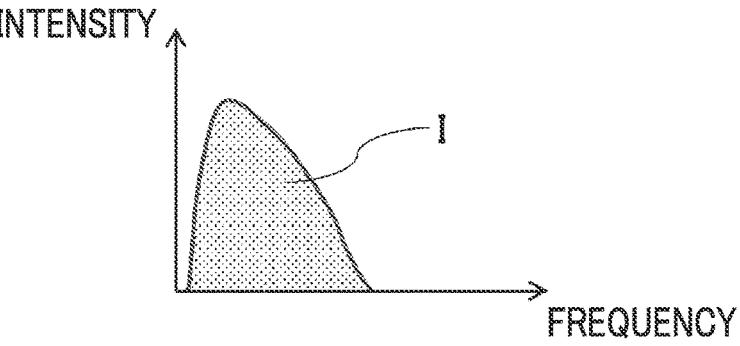
FIG. 4E is a diagram showing a frequency integrated value of a frequency spectrum in a region REBe of FIG. 2.

Since the ultrasound waves are attenuated in the subject, as shown in FIGS. 4A to 4C and 4E, for each region REB included in the evaluation range, as the depth is increased, the signal intensity of the reception beam data RB is gradually decreased, and the frequency integrated value I of the frequency spectrum also tends to be gradually decreased. In other words, since it can be said that the frequency integrated value I is an indicator of the attenuation of the ultrasound waves, the attenuation amount of the ultrasound waves can be estimated based thereon. It should be noted that, as shown in FIG. 4D, in the region REBd that is not included in the evaluation range, the frequency integrated value I of the frequency spectrum of the region REBd is a value that considerably deviates from a decrease tendency in the depth direction region row RRB due to the influence of the reflected waves or the like from a wall part of the structure. Therefore, the attenuation amount estimation unit 26 estimates the attenuation amount of the ultrasound waves by excluding the region REB that is not included in the evaluation range.

In addition, the attenuation amount estimation unit 26 can estimate the attenuation amount of the ultrasound waves based on a signal intensity slope representing a degree of decrease of the signal intensity toward the high frequency side in the frequency spectrum, of the region REB that is each region REB arranged in the depth direction and included in the evaluation range. FIGS. 5A to 5E are diagrams showing a signal intensity slope G of the frequency spectrum for each of the regions REBa to REBe shown in FIG. 2. The signal intensity slope G of each frequency spectrum is represented by a one-point chain line in FIGS. 5A to 5E.

Figure 5A:
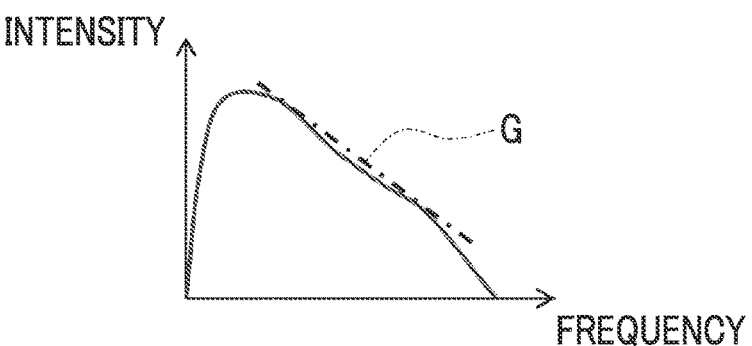
FIG. 5A is a diagram showing a signal intensity slope of the frequency spectrum in the region REBa of FIG. 2.
Figure 5B:
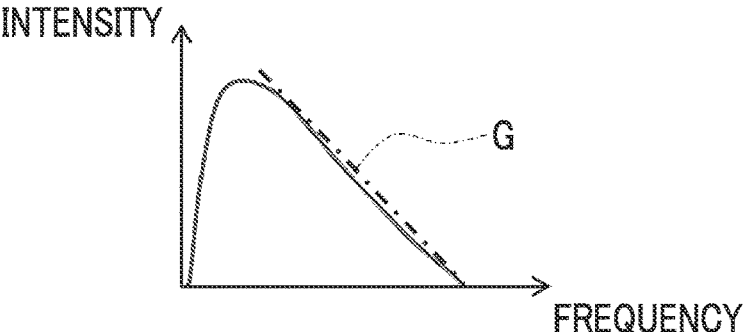
FIG. 5B is a diagram showing a signal intensity slope of the frequency spectrum in the region REBb of FIG. 2.
Figure 5C:
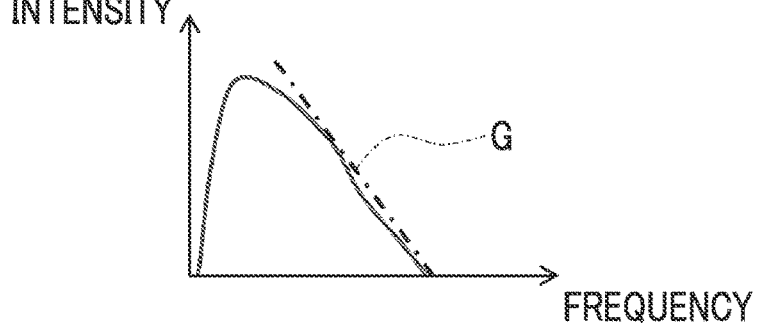
FIG. 5C is a diagram showing a signal intensity slope of the frequency spectrum in the region REBc of FIG. 2.
Figure 5D:
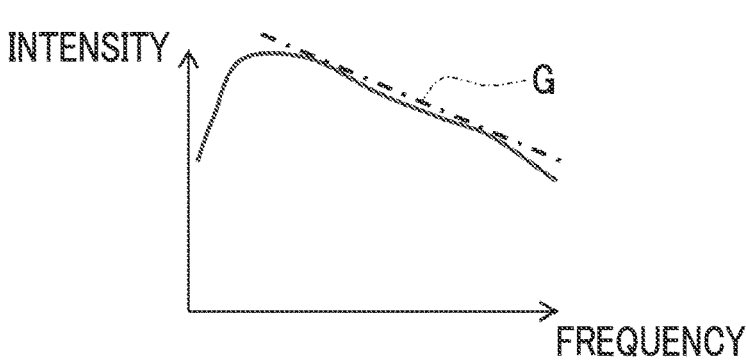
FIG. 5D is a diagram showing a signal intensity slope of the frequency spectrum in the region REBd of FIG. 2.
Figure 5E:
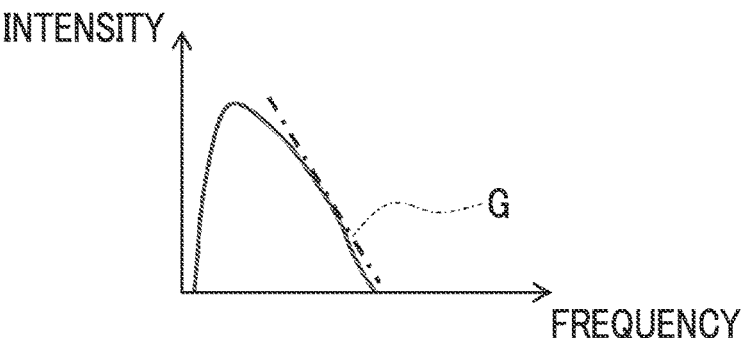
FIG. 5E is a diagram showing a signal intensity slope of the frequency spectrum in the region REBe of FIG. 2.

The ultrasound waves are attenuated in the subject, but the high frequency component is particularly attenuated. Therefore, as shown in FIGS. 5A to 5C and 5E, for each region REB included in the evaluation range, as the depth is increased, the high frequency component of the reception beam data RB is gradually removed, and as a result, an absolute value of the signal intensity slope G is gradually increased. In other words, since it can be said that the absolute value of the signal intensity slope G is an indicator of the attenuation of the ultrasound waves, the attenuation amount of the ultrasound waves can be estimated based thereon. It should be noted that, as shown in FIG. 5D, in the region REBd that is not included in the evaluation range, the absolute value of the signal intensity slope G of the frequency spectrum of the region REBd is a value that considerably deviates from an increase tendency in the depth direction region row RRB due to the influence of the reflected waves or the like from a wall part of the structure. Therefore, the attenuation amount estimation unit 26 estimates the attenuation amount of the ultrasound waves by excluding the region REB that is not included in the evaluation range.

In addition, the attenuation amount estimation unit 26 can estimate the attenuation amount of the ultrasound waves based on the cross point frequency in the frequency spectrum of the region REB that is each region REB arranged in the depth direction and included in the evaluation range. FIGS. 6A to 6E are diagrams showing a signal component S, a noise component N, and a cross point CP of the frequency spectrum for each of the regions REBa to REBe shown in FIG. 2.

Figure 6A:
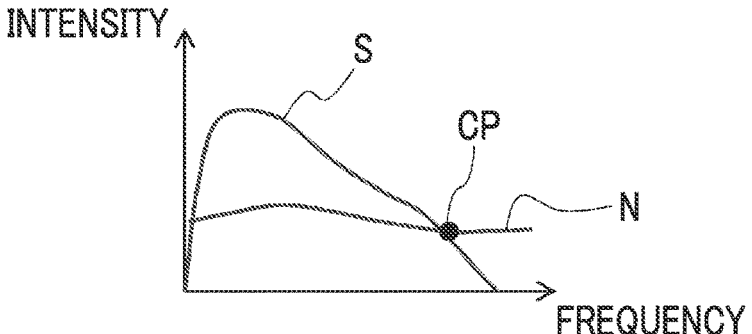
FIG. 6A is a diagram showing a signal component, a noise component, and a cross point of the frequency spectrum in the region REBa of FIG. 2.
Figure 6B:
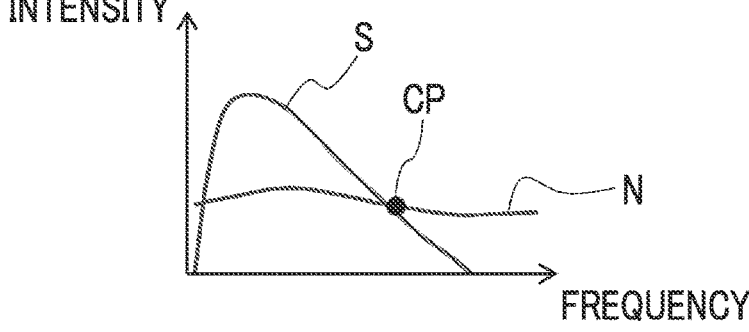
FIG. 6B is a diagram showing a signal component, a noise component, and a cross point of the frequency spectrum in the region REBb of FIG. 2.
Figure 6C:
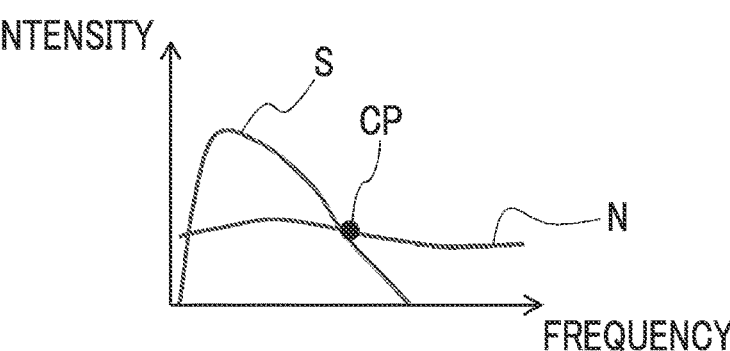
FIG. 6C is a diagram showing a signal component, a noise component, and a cross point of the frequency spectrum in the region REBc of FIG. 2.
Figure 6D:
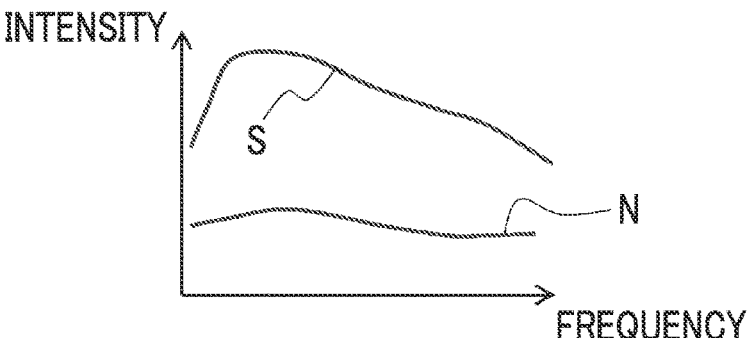
FIG. 6D is a diagram showing a signal component, a noise component, and a cross point of the frequency spectrum in the region REBd of FIG. 2.
Figure 6E:
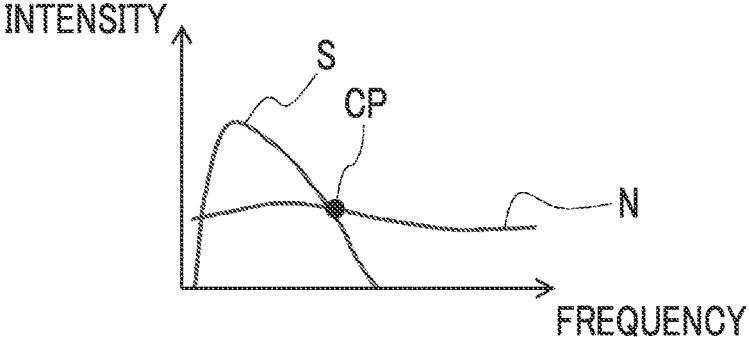
FIG. 6E is a diagram showing a signal component, a noise component, and a cross point of the frequency spectrum in the region REBe of FIG. 2.

As the ultrasound waves are attenuated in the subject, the high frequency component of the signal component S is particularly attenuated. On the other hand, a distribution of the frequency components of the noise component N (particularly, the electrical noise generated in the ultrasound probe 12 or the apparatus main body of the ultrasound diagnostic apparatus 10) is not changed so much depending on the depth. Therefore, as shown in FIGS. 6A to 6C and 6E, for each region REB included in the evaluation range, as the depth is increased, the high frequency component of the signal component S is gradually removed, and as a result, the cross point CP is gradually moved to the low frequency side. In other words, since it can be said that the cross point frequency is an indicator of the attenuation of the ultrasound waves, the attenuation amount of the ultrasound waves can be estimated based thereon. It should be noted that, as shown in FIG. 6D, in the region REBd that is not included in the evaluation range, since the signal component S is extremely increased (or decreased conversely) due to the influence of the reflected waves or the like from a wall part of the structure, the cross point frequency of the frequency spectrum of the region REBd is a value that considerably deviates from a decrease tendency in the depth direction region row RRB. Therefore, the attenuation amount estimation unit 26 estimates the attenuation amount of the ultrasound waves by excluding the region REB that is not included in the evaluation range.

It should be noted that the noise component N in each region REB can be the signal intensity of each region REB of the reception beam data RB output from the transmission/reception unit 14 in an environment in which each oscillation element of the ultrasound probe 12 does not receive the reflected waves from the subject (for example, in a case in which the ultrasound waves are transmitted toward air). Therefore, the noise component N of each region REB is acquired in advance, and stored in the memory 34. It is possible to acquire the signal component S by subtracting the noise component N from the signal intensity of the reception beam data RB.

In addition, the attenuation amount estimation unit 26 can estimate the attenuation amount of the ultrasound waves based on the representative frequency of the frequency spectrum of the region REB that is each region REB arranged in the depth direction and included in the evaluation range. FIGS. 7A to 7E are diagrams showing an average frequency AV as a representative frequency of the frequency spectrum for each of the regions REBa to REBe shown in FIG. 2. The average frequency AV of each frequency spectrum is represented by a one-point chain line in FIGS. 7A to 7E.

Figure 7A:
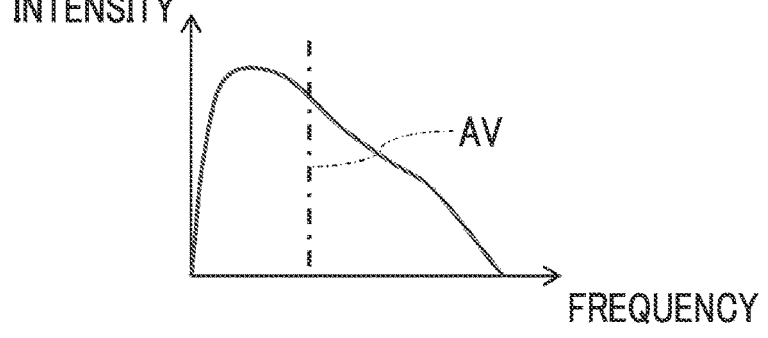
FIG. 7A is a diagram showing an average frequency of the frequency spectrum in the region REBa of FIG. 2.
Figure 7B:
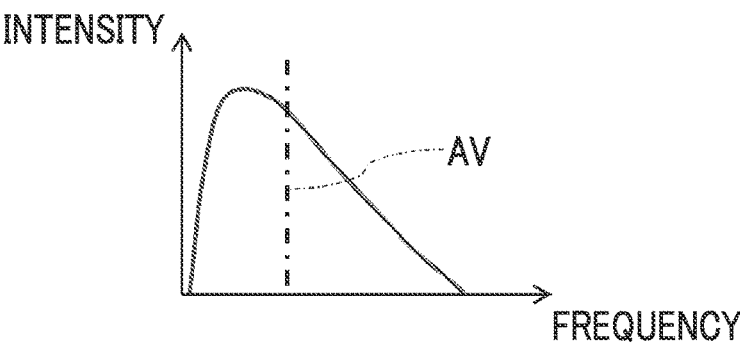
FIG. 7B is a diagram showing an average frequency of the frequency spectrum in the region REBb of FIG. 2.
Figure 7C:
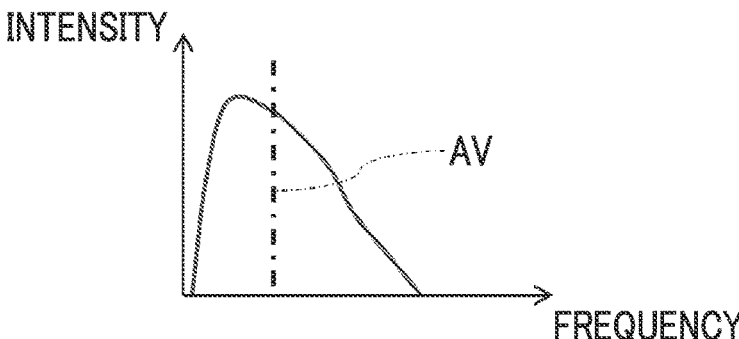
FIG. 7C is a diagram showing an average frequency of the frequency spectrum in the region REBc of FIG. 2.
Figure 7D:
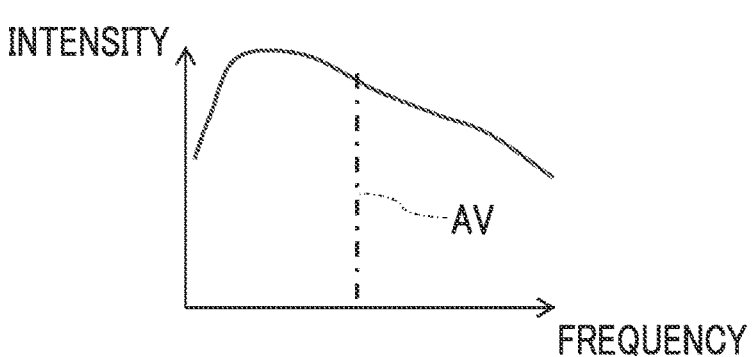
FIG. 7D is a diagram showing an average frequency of the frequency spectrum in the region REBd of FIG. 2.
Figure 7E:
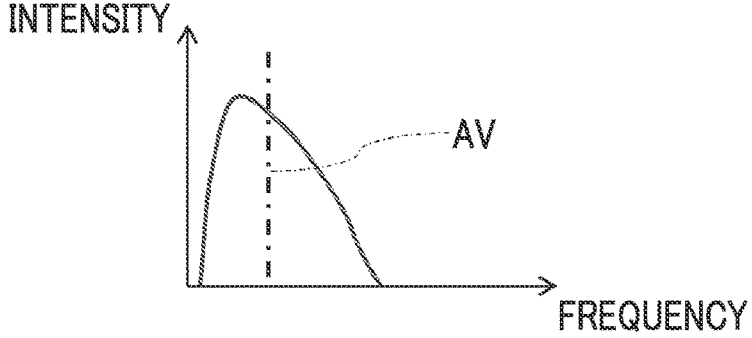
FIG. 7E is a diagram showing an average frequency of the frequency spectrum in the region REBe of FIG. 2.

The ultrasound waves are attenuated in the subject, but the high frequency component is particularly attenuated. Therefore, as shown in FIGS. 7A to 7C and 7E, for each region REB included in the evaluation range, as the depth is increased, the frequency spectrum is moved toward the low frequency side as a whole, and as a result, the average frequency AV tends to be gradually decreased. In other words, since it can be said that the average frequency AV is an indicator of the attenuation of the ultrasound waves, the attenuation amount of the ultrasound waves can be estimated based thereon. It should be noted that, as shown in FIG. 7D, in the region REBd that is not included in the evaluation range, since the signal intensity of the reception beam data RB is extremely increased (or decreased conversely) due to the influence of the reflected waves or the like from a wall part of the structure, the average frequency AV of the frequency spectrum of the region REBd is a value that considerably deviates from a decrease tendency in the depth direction region row RRB. Therefore, the attenuation amount estimation unit 26 estimates the attenuation amount of the ultrasound waves by excluding the region REB that is not included in the evaluation range.

It should be noted that, in the present embodiment, the representative frequency of the frequency spectrum is the average frequency AV, but the representative frequency is not limited to the average frequency AV, and may be, for example, a median frequency.

The attenuation amount estimation unit 26 estimates the attenuation amount of the ultrasound waves based on any one of the methods described above. Alternatively, the attenuation amount estimation unit 26 may estimate the attenuation amount of the ultrasound waves by combining the plurality of methods described above.

Figure 8:
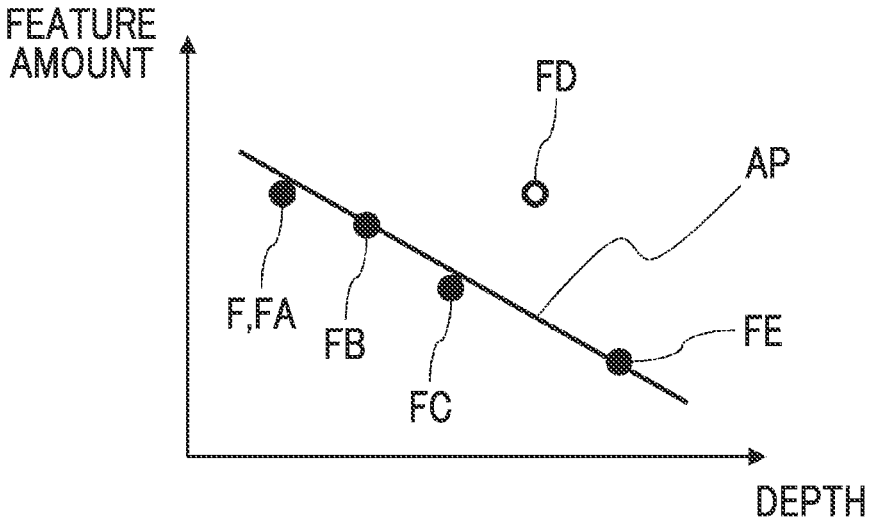
FIG. 8 is a first graph showing a relationship between a depth and a feature amount in a region row arranged in a depth direction.

Specifically, as shown in FIG. 8, the attenuation amount estimation unit 26 plots a feature amount F (feature amounts FA to FE in FIG. 8) of each region REB included in one depth direction region row RRB in a two-dimensional data space of the depth and the feature amount (frequency integrated value I, absolute value of signal intensity slope G, cross point frequency, or average frequency AV).

Here, the feature amount F (feature amount FD in FIG. 8) of the region REB that is not included in the evaluation range is excluded. Then, the attenuation amount estimation unit 26 calculates a function (including a quadratic function, a cubic function, or a function of a higher order) that approximates the remaining feature amounts FA, FB, FC, and FE, and sets a coefficient of the calculated function as the attenuation amount of the ultrasound waves. In the present embodiment, for the sake of simplicity, the attenuation amount estimation unit 26 generates an approximate straight line AP of the feature amounts FA, FB, FC, and FE, and sets an absolute value of a slope of the approximate straight line AP as the attenuation amount of the ultrasound waves. In a case in which the attenuation amount is estimated by combining the frequency integrated value I, the absolute value of the signal intensity slope G, the cross point frequency, or the average frequency AV, for example, an average value of the absolute values of the slopes of the plurality of approximate straight lines AP or the like can be set as the attenuation amount of the ultrasound waves based on a plurality of approximate straight lines AP calculated for each feature amount.

The attenuation amount estimation unit 26 calculates the attenuation amount (slope of the approximate straight line AP) of the ultrasound waves for each depth direction region row RRB. In some cases, the attenuation amounts of the ultrasound waves are different for each depth direction region row RRB, and in a case in which the TGC is performed based on the attenuation amount as it is, the brightness correction values may be different for each depth direction region row RRB. Therefore, the attenuation amount estimation unit 26 may estimate the frame attenuation amount corresponding to one frame based on the plurality of attenuation amounts estimated for the plurality of depth direction region rows RRB for one entire frame. The frame attenuation amount can be a representative value (for example, an average value) of the plurality of attenuation amounts estimated for the plurality of depth direction region rows RR for one frame.

The attenuation amount estimation unit 26 may estimate the frame attenuation amount based on a plurality of individual frame attenuation amounts for each of the plurality of frames, which are calculated based on the target beam data for the plurality of frames. For example, the attenuation amount estimation unit 26 can set a representative value (for example, an average value or a median value) of the plurality of individual frame attenuation amounts as the frame attenuation amount. As a result, the attenuation amount estimation unit 26 can estimate the frame attenuation amount in consideration of an error between the individual frame attenuation amounts for each frame.

In addition, the attenuation amount estimation unit 26 may decide the individual frame attenuation amount used for estimating the frame attenuation amount among the plurality of individual frame attenuation amounts based on statistics of the plurality of individual frame attenuation amounts for each of the plurality of frames. For example, as long as the ultrasound waves are transmitted to the same cross section of the same subject, each individual frame attenuation amount should indicate substantially the same value. Therefore, in a case in which the individual frame attenuation amount having a value considerably different from other individual frame attenuation amounts is calculated in the plurality of individual frame attenuation amounts, there is a high possibility that the individual frame attenuation amount does not indicate the correct attenuation amount. Therefore, the attenuation amount estimation unit 26 may estimate the frame attenuation amount by excluding such an individual frame attenuation amount.

For example, the attenuation amount estimation unit 26 calculates a representative value (average value, median value, or the like) of the plurality of calculated individual frame attenuation amounts. Then, a deviation, which is a difference between each individual frame attenuation amount and the calculated representative value, is calculated, and the individual frame attenuation amount in which the deviation is equal to or larger than a predetermined deviation threshold value is not used in the calculation of the frame attenuation amount. Stated another way, the attenuation amount estimation unit 26 calculates the frame attenuation amount based on the individual frame attenuation amount in which the deviation is less than the deviation threshold value.

Figure 9:
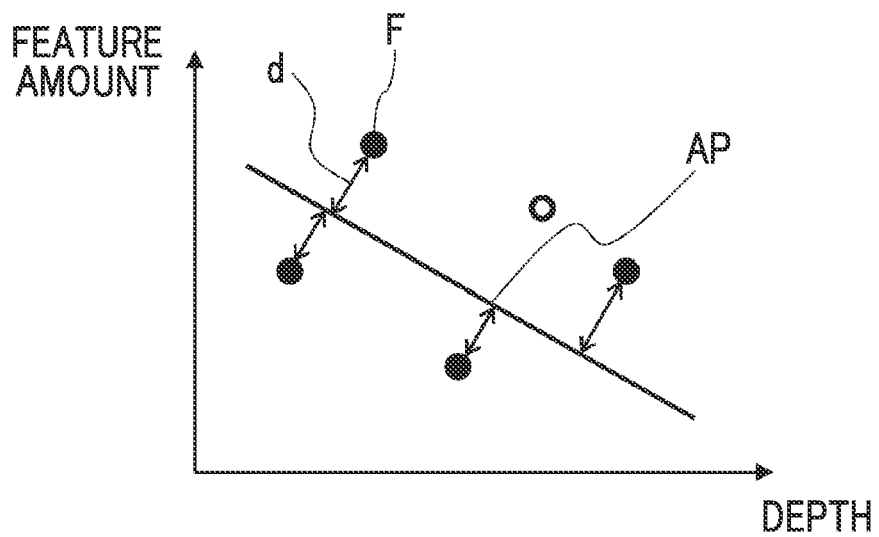
FIG. 9 is a second graph showing the relationship between the depth and the feature amount in the region row arranged in the depth direction.

As shown in FIG. 9, a case is also considered in which the feature amount F of each region REB included in one depth direction region row RRB and determined to be within the evaluation range does not show the decrease tendency (or increase tendency) and varies. Even in such a case, the approximate straight line AP can be generated, but there is no guarantee that the approximate straight line AP correctly represents the attenuation amount of the ultrasound waves. Therefore, in a case in which a plurality of feature amounts F calculated for the depth direction region row RRB satisfy a predetermined exclusion criterion, the attenuation amount estimation unit 26 may estimate the frame attenuation amount by excluding the depth direction region row RRB.

For example, the attenuation amount estimation unit 26 calculates a distance d between the generated approximate straight line AP and the feature amount F of each region REB within the evaluation range, and totals a plurality of distances d for each region REB. In a case in which the total value of the distances d is equal to or larger than a predetermined distance threshold value, the attenuation amount for the depth direction region row RRB is not used for estimating the frame attenuation amount.

TGC Processing

The image formation unit 20 executes the TGC processing based on the frame attenuation amount estimated by the attenuation amount estimation unit 26. In other words, the image formation unit 20 performs processing of transforming the brightness of each pixel of the ultrasound image according to the depth to compensate for the attenuation of the ultrasound waves indicated by the frame attenuation amount.

Figure 10:
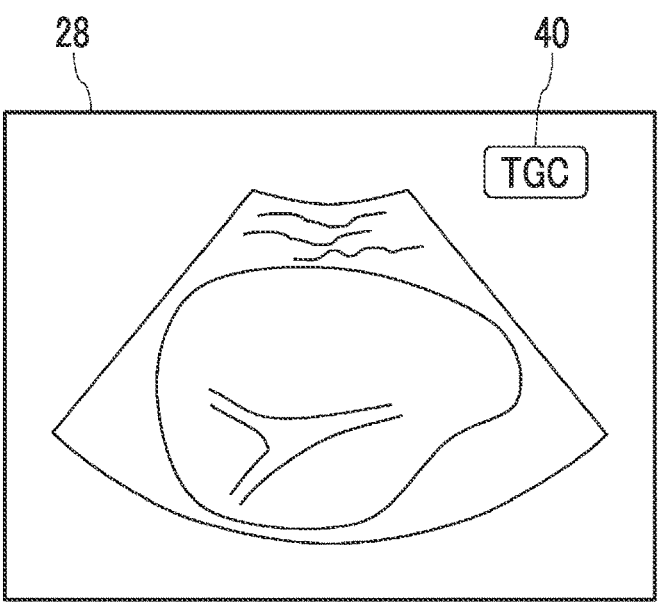
FIG. 10 is a diagram showing a display example of a TGC button.

The image formation unit 20 may execute the TGC processing at a timing at which the user of the ultrasound diagnostic apparatus 10 gives an instruction. For example, as shown in FIG. 10, the display controller 28 may display a TGC button 40 on the display 30, and the image formation unit 20 may execute the TGC processing with the operation of the TGC button 40 by the user as a trigger. A button for inputting the instruction for the TGC processing from the user may be provided in the input interface 32. In a case in which the TGC processing is always executed, the brightness of the B-mode image displayed on the display 30 may be changed (flicker) from moment to moment, which may make it difficult to see. By the image formation unit 20 executing the TGC processing in response to the instruction from the user, the user can execute the TGC processing at any timing, and can suppress flicker of the B-mode image.

In addition, in a case in which the ultrasound probe 12 is provided with the acceleration sensor, the image formation unit 20 can detect a change in the posture of the ultrasound probe 12 based on the signal from the acceleration sensor. In this case, the image formation unit 20 may execute the TGC processing in a case in which it is determined that the posture of the ultrasound probe 12 is stable. As a result, the TGC processing can be automatically executed in a case in which the user brings the ultrasound probe 12 into contact with the target position of the subject and maintains the contact.

Effects of Ultrasound Diagnostic Apparatus According to Present Embodiment

The outline of the ultrasound diagnostic apparatus 10 according to the present embodiment is described above. In the present embodiment, the evaluation range decision unit 24 excludes the region REB or the region REF including the structure in the subject from the evaluation range that is the target for estimating the attenuation amount of the ultrasound waves. As a result, in the TGC PROCESSING, the influence of the structure in the subject can be reduced. Further, in the present embodiment, the attenuation amount estimation unit 26 calculates the frequency spectrum of the reception beam data RB for each region REB having a certain width, and estimates the attenuation amount of the ultrasound image based on the frequency spectra of the plurality of regions REB arranged in the depth direction. As a result, in the TGC processing, the influence of the speckle can be reduced.

Flow of Processing of Ultrasound Diagnostic Apparatus

Figure 11:
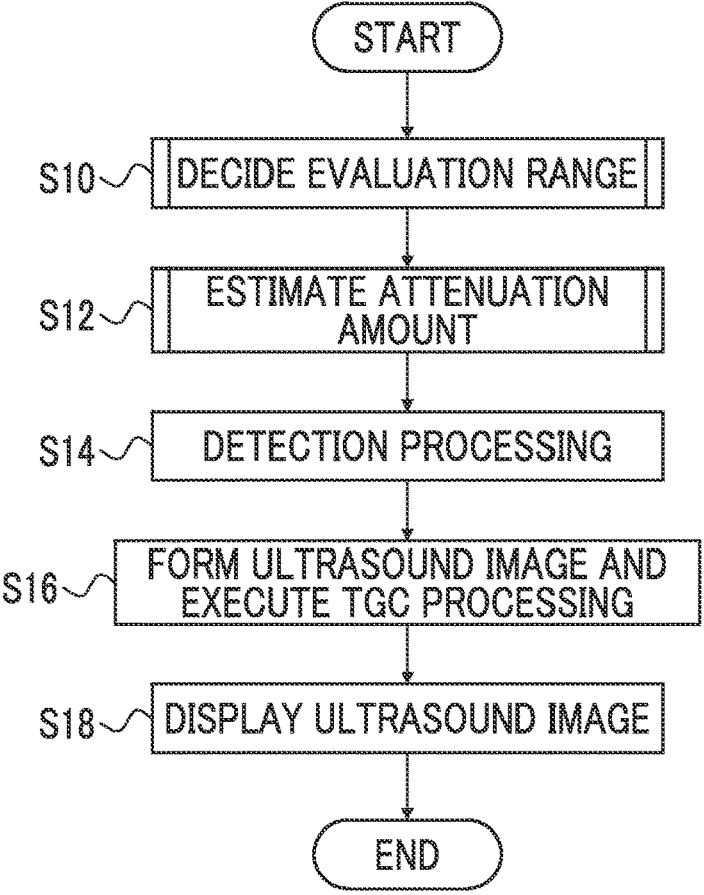
FIG. 11 is a flowchart showing a flow of processing of the ultrasound diagnostic apparatus according to the present embodiment.

Hereinafter, a flow of the processing of the ultrasound diagnostic apparatus 10 will be described with reference to the flowchart shown in FIGS. 11 to 13. FIG. 11 is a flowchart showing a flow of entire processing of the ultrasound diagnostic apparatus 10.

In step S10, the evaluation range decision unit 24 decides the evaluation range. A flow of decision processing of the evaluation range will be described later with reference to FIG. 12.

In step S12, the attenuation amount estimation unit 26 estimates the attenuation amount of the ultrasound waves. A flow of estimation processing of the attenuation amount of the ultrasound waves will be described later with reference to FIG. 13.

In step S14, the detection processing unit 18 executes the detection processing with respect to the reception beam data RB (particularly, the target beam data) from the signal processing unit 16. It should be noted that the processing of steps S10 and S12 and step S14 can be executed in parallel.

In step S16, the image formation unit 20 forms the ultrasound image (B-mode image) based on the reception beam data RB (particularly, the target beam data) after the detection processing. In addition, the image formation unit 20 executes the TGC processing in the formation processing of the ultrasound image or with respect to the formed ultrasound image, based on the attenuation amount of the ultrasound waves estimated in step S12.

In step S18, the display controller 28 displays the ultrasound image formed in step S16, on the display 30.

Figure 12:
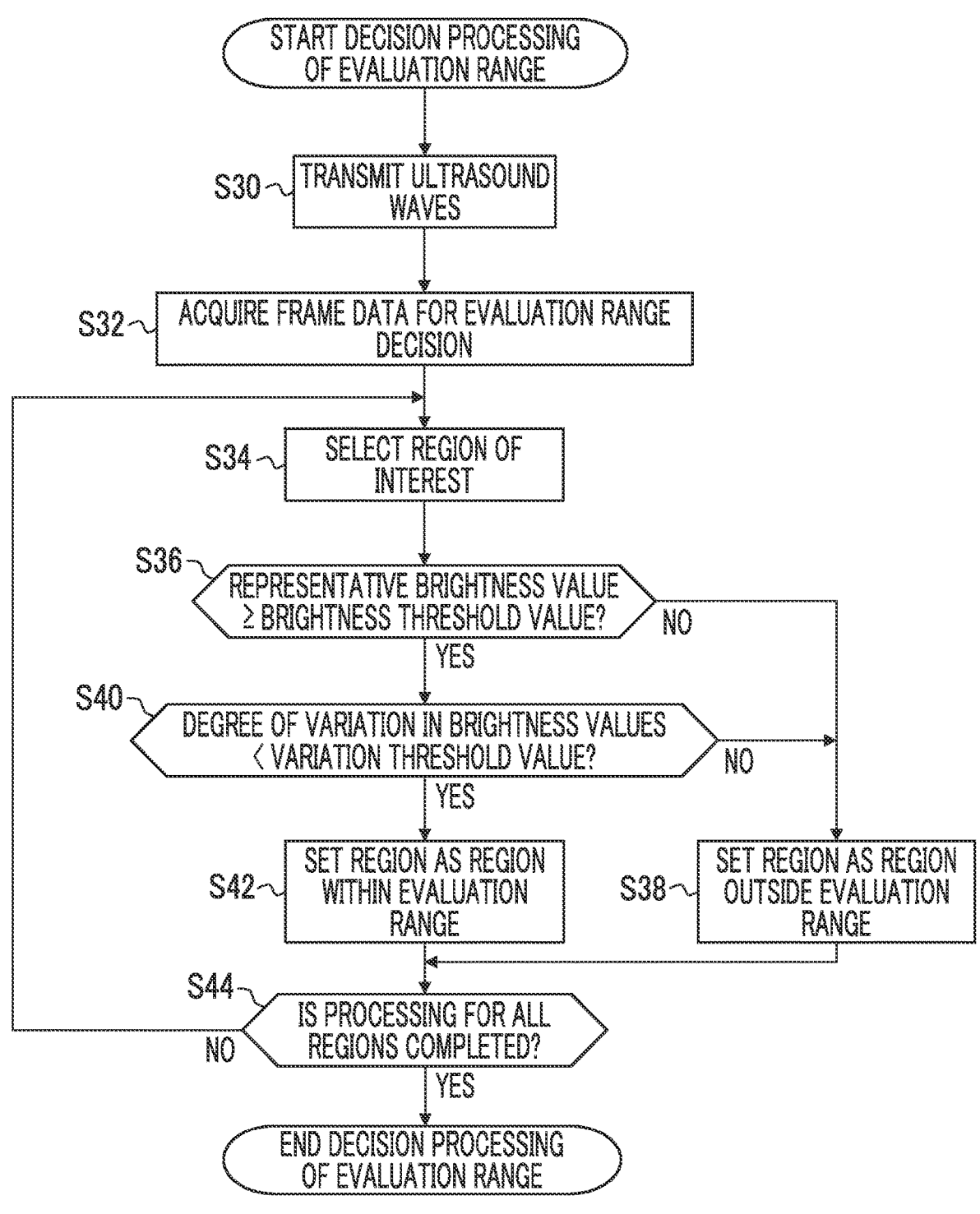
FIG. 12 is a flowchart showing a flow of decision processing of an evaluation range.

FIG. 12 is a flowchart showing a flow of the decision processing of the evaluation range.

In step S30, the transmission/reception unit 14 supplies the transmission signal to the ultrasound probe 12. As a result, the ultrasound waves are transmitted from the plurality of oscillation elements of the ultrasound probe 12 to the subject.

In step S32, the plurality of oscillation elements of the ultrasound probe 12 receive the reflected waves from the subject and transmit the reception signal to the transmission/reception unit 14. As a result, the transmission/reception unit 14 acquires the reception signal. The transmission/reception unit 14 performs the reception beam forming with respect to the reception signal to form the reception beam data for evaluation range decision. The frame data for evaluation range decision is formed by the detection processing of the reception beam data for evaluation range decision by the detection processing unit 18. The frame data for evaluation range decision is stored in the cine memory 22.

In step S34, the evaluation range decision unit 24 selects a region of interest among the plurality of regions REF defined in advance in the data space of the frame data FR.

In step S36, the evaluation range decision unit 24 calculates the representative brightness value (for example, the average brightness value) of the brightness values of the plurality of pixels included in the region of interest selected in step S34. Then, the evaluation range decision unit 24 determines whether or not the calculated representative brightness value is equal to or larger than the predetermined brightness threshold value. In a case in which the representative brightness value is less than the brightness threshold value, there is a high possibility that the region of interest is, for example, the region REF included in the blood vessel. Therefore, in this case, the processing proceeds to step S38, and the evaluation range decision unit 24 sets the region REF as the region REF outside the evaluation range. In a case in which the representative brightness value is equal to or larger than the brightness threshold value, the processing proceeds to step S40.

In step S40, the evaluation range decision unit 24 calculates the degree of variation (for example, the standard deviation) of the brightness values of the plurality of pixels included in the region of interest selected in step S34. Then, the evaluation range decision unit 24 determines whether or not the calculated degree of variation is less than the predetermined variation threshold value. In a case in which the degree of variation is equal to or larger than the variation threshold value, there is a high possibility that an object is included in the region of interest. Therefore, in this case, the processing proceeds to step S38, and the evaluation range decision unit 24 sets the region REF as the region REF outside the evaluation range. In a case in which the degree of variation is less than the variation threshold value, the processing proceeds to step S42.

In step S44, the evaluation range decision unit 24 sets the region REF as the region REF within the evaluation range.

It is determined in step S44 whether or not the processing of steps S34 to S42 is performed for all the regions REF. In a case in which the region REF for which the processing is not executed remains, the processing returns to step S34, and the evaluation range decision unit 24 selects another region REF as the region of interest. In a case in which the processing for all the regions REF is completed, the decision processing of the evaluation range ends.

Figure 13:
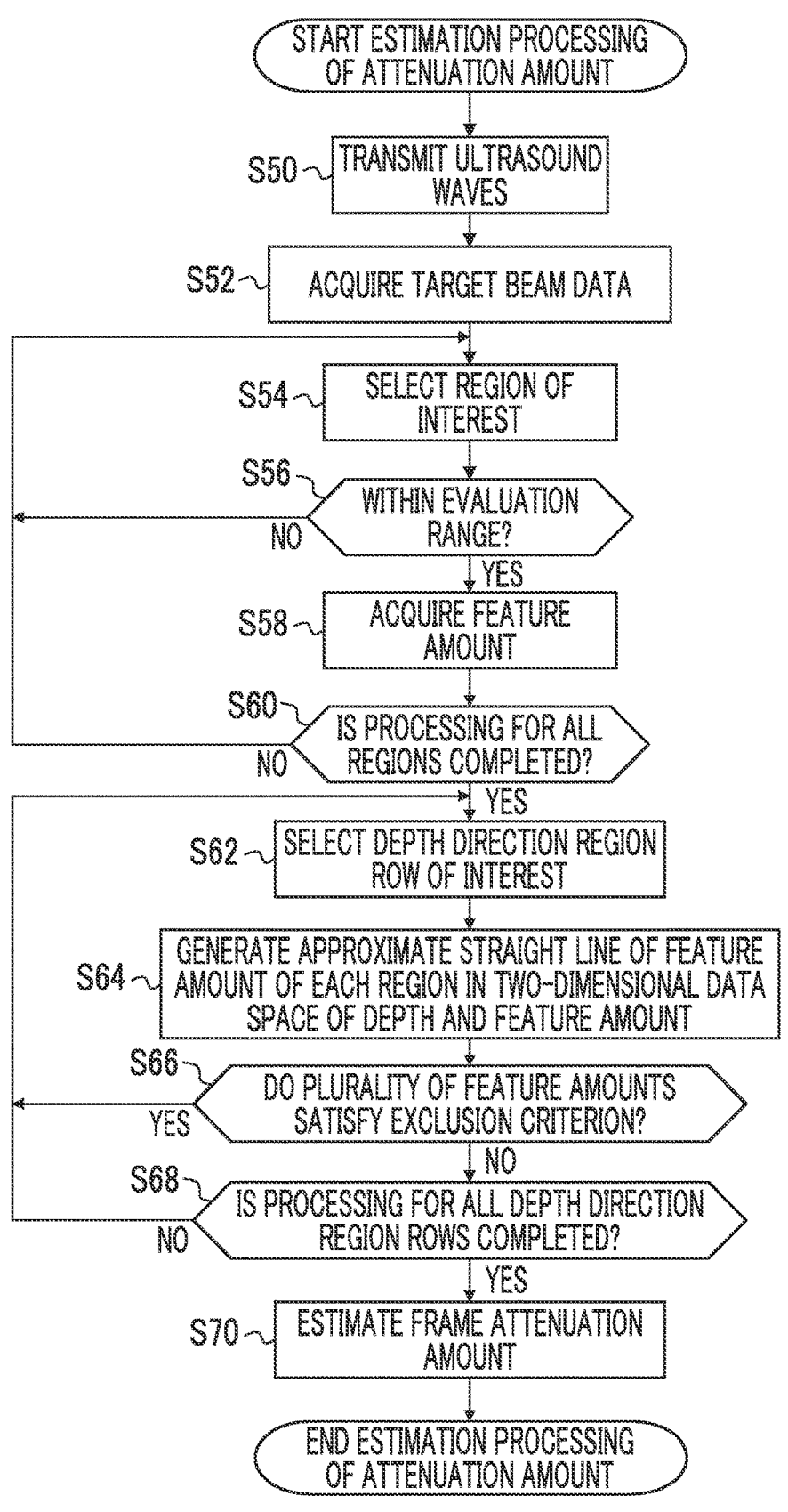
FIG. 13 is a flowchart showing a flow of estimation processing of an attenuation amount.

FIG. 13 is a flowchart showing a flow of the estimation processing of the attenuation amount.

In step S50, the transmission/reception unit 14 supplies the transmission signal to the ultrasound probe 12. As a result, the ultrasound waves are transmitted from the plurality of oscillation elements of the ultrasound probe 12 to the subject.

In step S52, the plurality of oscillation elements of the ultrasound probe 12 receive the reflected waves from the subject and transmit the reception signal to the transmission/reception unit 14. As a result, the transmission/reception unit 14 acquires the reception signal. The transmission/reception unit 14 performs the reception beam forming with respect to the reception signal to form the target beam data following the reception beam data for evaluation range decision in time series.

In step S54, the attenuation amount estimation unit 26 selects the region of interest among the plurality of regions REB defined in advance in the data space of the reception beam data RB.

In step S56, the attenuation amount estimation unit 26 determines whether or not the region of interest selected in step S54 is within the evaluation range. In a case in which the selected region of interest is outside the evaluation range, the processing returns to step S54, and the attenuation amount estimation unit 26 selects another region REB as the region of interest. In a case in which the selected region of interest is within the evaluation range, the processing proceeds to step S58.

In step S58, the attenuation amount estimation unit 26 executes the FFT with respect to the reception beam data RB in the region of interest. As a result, the frequency spectrum of the reception beam data RB for the region of interest is acquired. Next, the attenuation amount estimation unit 26 acquires the feature amount (frequency integrated value I, absolute value of signal intensity slope G, cross point frequency, average frequency AV, or the like described above) of the acquired frequency spectrum.

In step S60, the attenuation amount estimation unit 26 determines whether or not the processing of steps S54 to S58 is performed for all the regions REB. In a case in which the region REB for which the processing is not executed remains, the processing returns to step S54. In a case in which the processing for all the regions REB is completed, the processing proceeds to step S62. By the processing of steps S54 to S60, the feature amount for the region REB within the evaluation range is acquired.

In step S62, the attenuation amount estimation unit 26 selects a depth direction region row of interest among the plurality of depth direction region rows RRB.

In step S64, the attenuation amount estimation unit 26 plots the feature amount for each region REB included in the selected depth direction region row of interest and included in the evaluation range in the two-dimensional data space of the depth and the feature amount (see FIG. 8). Then, the approximate straight line AP of each of the plotted feature amounts is generated.

In step S66, the attenuation amount estimation unit 26 determines whether or not the feature amount for each region REB included in the selected depth direction region row of interest and included in the evaluation range satisfies the predetermined exclusion criterion. In a case in which the exclusion criterion is satisfied, the attenuation amount estimation unit 26 does not use the depth direction region row of interest for estimating the frame attenuation amount, returns to step S62, and selects another depth direction region row of interest. In a case in which the exclusion criterion is not satisfied, the absolute value of the slope of the approximate straight line AP generated in step S64 is estimated as the attenuation amount of the ultrasound waves in the depth direction region row of interest. Then, the processing proceeds to step 68.

It is determined in step S68 whether or not the processing of steps S62 to S66 is performed for all the depth direction region rows RRB for one frame. In a case in which the depth direction region row RRB for which the processing is not executed remains, the processing returns to step S62. In a case in which the processing for all the depth direction region rows RRB is completed, the processing proceeds to step S70. By the processing of steps S62 to S66, the attenuation amount of the ultrasound waves for all the depth direction region rows RRB is acquired.

In step S70, the attenuation amount estimation unit 26 estimates the frame attenuation amount corresponding to one frame based on the plurality of attenuation amounts estimated for the plurality of depth direction region rows RRB for one frame. For example, the attenuation amount estimation unit 26 sets the average value of the plurality of attenuation amounts estimated for the plurality of depth direction region rows RRB for one frame as the frame attenuation amount.

Although the embodiment according to the present invention has been described above, the present invention is not limited to the embodiment described above, and various modifications can be made without departing from the gist of the present invention.

For example, in the present embodiment, the ultrasound probe 12 is the probe including the oscillation elements arranged in a row, but the ultrasound probe 12 may be a two-dimension (2D) array probe including oscillation elements arranged in two dimensions. The reception beam data, which is the processing target of each of the units of the ultrasound diagnostic apparatus 10, may constitute three-dimensional volume data obtained by the 2D array probe and extending in the depth direction, an azimuth direction, and a slice direction.

What is claimed is:

1. An ultrasound diagnostic apparatus comprising:
a hardware processor configured to:
analyze frame data for evaluation range decision formed based on reception beam data for the evaluation range decision, to decide an evaluation range excluding at least a part of a structure in the subject in a data space of the frame data, wherein the reception beam data is formed by reception beam forming with respect to a reception signal obtained by transmitting and receiving ultrasound waves to and from a subject, and the evaluation range decision decides whether each region in the data space of the frame data is included in the evaluation range or excluded from the evaluation range;
estimate an attenuation amount of the ultrasound waves based on first target beam data that are reception beam data following the reception beam data for the evaluation range decision in time series, wherein the attenuation amount of the ultrasound waves is estimated based only on a frequency spectrum of second target beam data of each region included in the evaluation range among a plurality of regions arranged in a depth direction of the subject defined in advance in a data space of the reception beam data, wherein the second target beam data of each region is a part of the first target beam data;
execute an envelope detection processing on the first target beam data to generate third target beam data; and
form an ultrasound image based on the third target beam data, and execute a brightness correction processing based on the attenuation amount of the ultrasound waves, to compensate for brightness of each pixel of the ultrasound image which is decreased due to attenuation of the ultrasound waves.

2. The ultrasound diagnostic apparatus according to claim 1,
wherein the hardware processor further configured to decide the evaluation range based on, for each region in the data space of the frame data corresponding to each region in the data space of the reception beam data, at least one of a degree of variation in brightness values of a plurality of pixels included in the region in the frame data for the evaluation range decision or a representative brightness value of the plurality of pixels included in the region.

3. The ultrasound diagnostic apparatus according to claim 1,
wherein the hardware processor further configured to estimate the attenuation amount based on at least one of a frequency integrated value of signal intensity in the frequency spectrum, a signal intensity slope representing a degree of decrease of the signal intensity toward a high frequency side in the frequency spectrum, a cross point frequency that is a frequency at which signal intensity of a signal component and signal intensity of a noise component in the frequency spectrum are the same as each other, or a representative frequency of the signal component in the frequency spectrum of each region arranged in the depth direction.

4. The ultrasound diagnostic apparatus according to claim 1,
wherein the hardware processor further configured to estimate the attenuation amount for each region row arranged in the depth direction, to estimate a frame attenuation amount corresponding to one entire frame based on a plurality of the attenuation amounts estimated for a plurality of the region rows for one frame.

5. The ultrasound diagnostic apparatus according to claim 4,
wherein the hardware processor further configured to estimate the frame attenuation amount based on a plurality of individual frame attenuation amounts for each of a plurality of frames.

6. The ultrasound diagnostic apparatus according to claim 5,
wherein the hardware processor further configured to decide the individual frame attenuation amount used for estimating the frame attenuation amount among the plurality of individual frame attenuation amounts based on statistics of the plurality of individual frame attenuation amounts for each of the plurality of frames, wherein the statistics of the plurality of individual frame attenuation amounts comprises average value or median value.

7. The ultrasound diagnostic apparatus according to claim 1, wherein the hardware processor further configured to execute the brightness correction processing at a timing at which an instruction is given from a user.

8. The ultrasound diagnostic apparatus according to claim 1, wherein the hardware processor further configured to execute the brightness correction processing in a case in which it is determined that a posture of an ultrasound probe that transmits and receives the ultrasound waves to and from the subject is stable.

\* \* \* \* \*